United States Patent
Garcines et al.

(10) Patent No.: US 9,295,723 B2
(45) Date of Patent: Mar. 29, 2016

(54) ACNE SOLUTION

(71) Applicant: Envy Medical, Inc., Westlake Village, CA (US)

(72) Inventors: Lyndon Garcines, Fountain Valley, CA (US); Susan Goldsberry, Huntington Beach, CA (US); Senad Ibrulj, Santa Ana, CA (US)

(73) Assignee: Envy Medical, Inc., Westlake Village, CA (US)

( * ) Notice: Subject to any disclaimer, the term of this patent is extended or adjusted under 35 U.S.C. 154(b) by 0 days.

(21) Appl. No.: 13/783,066

(22) Filed: Mar. 1, 2013

(65) Prior Publication Data

US 2014/0249116 A1 Sep. 4, 2014

(51) Int. Cl.
| | |
|---|---|
| A61K 45/06 | (2006.01) |
| A61K 9/08 | (2006.01) |
| A61K 47/38 | (2006.01) |
| A61K 31/045 | (2006.01) |
| A61K 31/05 | (2006.01) |
| A61K 31/60 | (2006.01) |
| A61K 36/487 | (2006.01) |
| A61K 36/535 | (2006.01) |
| A61K 36/63 | (2006.01) |

(52) U.S. Cl.
CPC . *A61K 45/06* (2013.01); *A61K 9/08* (2013.01); *A61K 31/045* (2013.01); *A61K 31/05* (2013.01); *A61K 31/60* (2013.01); *A61K 36/487* (2013.01); *A61K 36/535* (2013.01); *A61K 36/63* (2013.01); *A61K 47/38* (2013.01)

(58) Field of Classification Search
CPC combination set(s) only.
See application file for complete search history.

(56) References Cited

U.S. PATENT DOCUMENTS

| | | | |
|---|---|---|---|
| 2008/0069898 A1* | 3/2008 | Smith et al. | 424/642 |
| 2009/0137534 A1 | 5/2009 | Chaudhuri | |
| 2010/0040696 A1* | 2/2010 | Sente et al. | 424/497 |
| 2012/0058167 A1 | 3/2012 | Widgerow | |
| 2012/0093755 A1* | 4/2012 | Humphreys et al. | 424/70.14 |
| 2012/0201769 A1* | 8/2012 | Hong | A61K 31/05 424/62 |
| 2012/0271251 A1 | 10/2012 | Webb | |

FOREIGN PATENT DOCUMENTS

WO WO 2008143761 A1 * 11/2008

OTHER PUBLICATIONS

Acunutrol TM Gel, Topical gel designed to support acute skin and acne conditions, Designs for Health [retrieved from on-line website: http://mkt.s.designsforhealth.com/Label_PDF/AcnutrolGel-Techsheet.pdf, last visit Oct. 19, 2015].*
Chahuri, et al., "Bakuchiol in the management of acne-affected skin," Cosmetics and Toiletries Magazine, 2011, vol. 126, No. 7, pp. 502-510.
International Search Report, PCT Application PCT/US2014/020017, Jun. 26, 2014, 3 pages.
Written Opinion, PCT Application PCT/US2014/020017, Jun. 26, 2014, 7 pages.
Sodhala Sodhalanighantaub 5 pp. (p. No. 4-8) ( Ref. p. No. of publication: 106 ) Edn 1st 1978 Oriental Institute Baroda, India.†
Ziya Al-Din Andullah Ibn Al-Baitar Al-Jaam'e-li-Mufradaat-al-Advia-wal-Aghzia. vol. IV (13th century AD) 6 pp. (p. No. 9-14) (Ref. p. No. of publication:6) 1874 AD Matba Amra Cairo, Egypt.†
Mohammad Akmal Khan Qaraabaadeen Azam wa Akmal 4 pp. (p. No. 15-18) (Ref. p. No. of publication:347) 1909 AD Matba Siddiqi. Delhi/Matba Mustafai Delhi, India.†

* cited by examiner
† cited by third party

*Primary Examiner* — Ernst V Arnold
*Assistant Examiner* — Kyung Sook Chang
(74) *Attorney, Agent, or Firm* — Aka Chan LLP

(57) ABSTRACT

A composition for the treatment of acne includes hydrolyzed *Psoralea Corylifolia*, containing a component bakuchiol, is solubilized in a water-based solution. The composition is for topical application to the skin. In a specific implementation, the composition is a water-based acne gel. In a specific implementation, a composition includes Bakutrol™, which includes bakuchiol, and bisabolol. The composition can include a polysorbate surfactant. In implementations, these ingredients are combined with other active ingredients, including for example, salicylic acid. A process of preparation of the composition allows for the stabilization of Bakutrol in solution.

15 Claims, No Drawings

ACNE SOLUTION

BACKGROUND OF THE INVENTION

The invention relates to the field of skincare compositions and more specifically to compositions for treating acne vulgaris.

Acne vulgaris (acne) is a chronic inflammatory condition of the pilosebaceous units of the skin, which is particularly prevalent in adolescents. The condition generally causes the formation, on the skin, of comedones, red papules, pustules and sometimes cysts. This is unsightly and furthermore, if untreated, acne can lead to scarring of the skin. The major causes of acne are thought to be an increase in sebum production, an increased presence of Proprionibacterium acnes (P. acne), blockage of the pilosebaceus duct and the production of inflammation.

Typical treatments for acne include therapies containing benzoyl peroxide, retinoids or a combination of an antibiotic and benzoyl peroxide. However, these therapies are harsh on the skin and can cause excessive dryness, redness, irritation, and peeling. These therapies can take between 3 to 6 weeks to reduce inflammatory acne lesions by fifty percent. The amount of time its takes for typical acne treatment products to work and the tolerability issues they present, cause users to be non-compliant in using these products as prescribed; experience little to no reduction in acne; and be less likely to re-purchase the acne products.

There is a continuing demand for acne treatment therapies that are more effective and potent, and easy to use, while minimizing harsh side effects on the skin. Therefore, there is a need for improved treatment products for acne.

BRIEF SUMMARY OF THE INVENTION

The present invention is directed to a composition and process of preparation of a compound for the treatment of acne. The compound is for topical application to the skin. Specifically, the composition includes Bakutrol™, containing the ingredient bakuchiol, that is solubilized in a water-based solution.

In a specific implementation, a composition includes hydrolyzed *Psoralea Corylifolia* containing bakuchiol as a primary component (or Bakutrol), and bisabolol. The composition can include a preservative, a surfactant, an emollient, or a combination. In a specific implementation, Bakutrol and bisabolol RAC are combined with polysorbate 20 as the preservative. In implementations, these ingredients are combined with other active ingredients, including for example, salicylic acid.

In a specific implementation, a composition includes Bakutrol, bisabolol, polysorbate 20, and other ingredients: salicylic acid, olea europaea (olive) fruit extract, perilla ocymoides leaf extract (e.g., shiso extract powder), sodium PCA, hydroxyethylcellulose, disodium EDTA, gluconolactone, lactic acid, sodium benzoate, dextrin, water, glycolic acid, sodium hydroxide, and butylene glycol. In other implementations, the composition can include Bakutrol and any one or more of the ingredients, in any combination.

The present invention includes a method of preparation of a water-based acne gel composition. The preparation solubilizes Bakutrol which allows it to be effectively absorbed by the skin, and allows it to be stable in the gel. The gel is effective in reducing inflammatory acne lesions by 50 percent in as few as about 7 days with a 90 percent reduction achieved in about 14 days. Unlike typical prescription and over-the-counter acne treatments, the gel does not cause collateral damage to the skin, including dry skin, skin irritation, redness, and peeling.

Other objects, features, and advantages of the present invention will become apparent upon consideration of the following detailed description and the accompanying drawings, in which like reference designations represent like features throughout the figures.

DETAILED DESCRIPTION OF THE INVENTION

Acne is a common skin condition, characterized by areas of skin with seborrhea (scaly red skin), comedones (blackheads and whiteheads), papules (pinheads), pustules (pimples), nodules (large papules) and possibly scarring.

Approximately 650 million people worldwide, or about 9.4 percent of the world population, experience some degree of acne. In the United States alone, acne affects about 40 to 50 million people annually. Research has shown that about 85% of young people between the ages of 12 and 24 years have acne, and while it is most common in teenagers, acne affects 8 percent of adults aged 25 to 34 years and 3 percent of adults aged 35 to 44 years.

Modern societies place a great emphasis on physical appearance. Although acne is not a life-threatening condition, it has significant physical and psychological ramifications such as permanent scarring, poor self image and self esteem, social phobia, social dysfunction, depression, anxiety, suicide, and overall reduced quality of life. Therefore, acne should be regarded as a serious medical disorder.

The available topical agents for the treatment of acne typically include benzoyl peroxide, retinoids, antibiotics, antiseborrheic medications, antiandrogen medications, hormonal treatments, salicylic acid, alpha hydroxy acid, and a combination of these. The therapeutic success in acne of these treatments is highly dependent on a regular application of the topical agents over a prolonged period of time. However, disadvantages associated with these commonly used topical agents considerably affect patient compliance and obstruct the treatment. These agents can cause undesirable side effects such as excessive dryness, redness, irritation and peeling. In addition, the use of antibiotics has limitations due to development of resistance by bacteria. The use of retinoids has also been linked to causing developmental malformations.

These agents can take long periods of time to work. Research has shown that even effective prescription and over-the-counter acne treatment products can take up to between 3 to 6 weeks to reduce inflammatory acne lesions by about 50 percent. These and other disadvantages can cause users to be non-compliant in using acne products as prescribed.

Bakutrol™ is an antimicrobial and anti-inflammatory agent that has been shown to help reduce the bacterial activity, inflammation, and scarring seen in acne. Bakutrol is a trademark of Unigen, Inc. Any trademarks listed in this patent application are the property of their respective owners. Bakutrol is a natural, botanical agent. It contains bakuchiol, a natural phenol isolated from the seeds of *Psoralea corylifolia* or *Psoralea glandulosa*, a tree native to China known for its uses in traditional Chinese medicine.

Bakuchiol has a natural ability to fight inflammation, by controlling leukocytic functions at the site of the inflammation. In clinical studies, Bakutrol reduced both inflammatory and non-inflammatory acne lesions without the adverse side effects often found with harsh chemicals. Bakuchiol also possesses protective antioxidant characteristics due to its scavenging activity against oxidative damage to lipids and proteins. Additionally, Bakutrol significantly reduces scarring or Post-Inflammatory Hyperpigmentation (PIH), the dark spots left behind long after the acne lesion has healed. Unlike traditional acne treatments, Bakutrol has been clinically proven to reduce PIH. In studies, bakuchiol has been shown to be more potent at treating acne than benzoyl peroxide.

Research on bakuchiol demonstrates its ability to inhibit both the growth of acne-causing bacteria and the COX/LOX inflammatory pathways. Bakuchiol has also been shown to regulate sebum production. A pilot study on subjects with a diagnosis of facial acne vulgaris showed significant reductions in inflammatory (papules, cysts) and non-inflammatory (blackheads) lesions (Yaping, E, et al, SUNY Downstate Medical Center, Brooklyn, N.Y.). Forty-five percent of these study subjects also experienced partial or total clearing of acne-related post-inflammatory hyperpigmentation (PIH) which can follow acne vulgaris and results in skin melanosis (dark pigmentation).

Hydrolyzed *Psoralea Corylifolia*, containing bakuchiol, is naturally insoluble in water. The hydrolysis of *Psoralea Corylifolia* extracts the component bakuchiol, which is contained in Bakutrol. It is very difficult to incorporate Bakutrol into a water-based gel preparation for topical use since it is insoluble. Some prescription and over-the-counter acne products contain suspended particles of bakuchiol that are very large and cannot penetrate into sebaceous follicles (pores). The skin cannot absorb these products even when excess amounts of bakuchiol are present. These products are therefore, ineffective at delivering bakuchiol to the dermal tissue. Furthermore, due to bakuchiol's inability to solubilize in water, bakuchiol can become unstable in aqueous solutions.

The present invention uses novel technology including a unique formulation and preparation that solubilizes bakuchiol (Bakutrol), without the use of alcohol. When Bakutrol is solubilized, it can be effectively delivered into the sebaceous follicles (pores) with bisabolol where these ingredients, with salicylic acid, can promote rapid clinical results. Solubilized Bakutrol can be easily absorbed by the skin. Hence, the skin treatment properties of Bakutrol are significantly enhanced when it is solubilized according to the present invention.

Bisabolol is the main active ingredient of the medical plant chamomile (*Matricaria chamomilla*). Bisabolol protects and heals the skin from the effects of daily stress. It is a naturally occurring active ingredient that accelerates the healing process of skin. Research has shown that it contains anti-inflammatory properties.

In a specific implementation, a composition includes hydrolyzed *Psoralea Corylifolia*, containing bakuchiol as its primary component (or Bakutrol) and bisabolol. The composition can include a polysorbate surfactant, which is a stable and relatively nontoxic agent that allows it to be used as a detergent and emulsifier in a number of domestic, scientific, and pharmacological applications. In pharmaceutical applications, it is used to stabilize emulsions and suspensions. In a specific implementation, Bakutrol and bisabolol RAC is combined with polysorbate 20 as the emollient.

In a specific implementation, a composition includes Bakutrol, bisabolol, polysorbate 20, and other ingredients: salicylic acid, olea europaea (olive) fruit extract, perilla ocymoides leaf extract (e.g., shiso extract powder), sodium PCA, hydroxyethylcellulose, disodium EDTA, gluconolactone, lactic acid, sodium benzoate, dextrin, water, glycolic acid, sodium hydroxide, and butylene glycol. In other implementations, the composition can include Bakutrol and any one or more of the ingredients, in any combination. Other ingredients (and their equivalents) can be substituted for or replace any of the one or more of the listed ingredients. For example, polysorbate 20 can be replaced by caprylyl glycol, ethylhexylglycerin, or PPG-2 isoceteth-20 acetate.

Research has shown that there is a synergistic effect in solubilizing Bakutrol, rather than an additive effect, when combinations of the ingredients listed above are combined. In a mixture of ingredients, each ingredient works through a specific mechanism of action, and has an individual effect when combined with Bakutrol. An additive effect of the mixture is the same as the sum of the individual effects of each ingredient. In contrast, a synergistic effect of a mixture of substances is greater than the sum of the individual effects. For example, Compounds A and B each has a solubility rate of 10 percent when used individually. However in combination, the actual combined solublity rate is 30 percent, rather than an anticipated additive effect of 20 percent, resulting in an enhancement of 10 percent. The combinations of ingredients, such as those presented above, have been shown to produce this synergistic effect. In combination, the solubility of Bakutrol is amplified. Consequently, the combination of ingredients can be effective in solubilizing and stabilizing Bakutrol, while optimizing the benefits of Bakutrol, and can increase the duration of time of stability of the Bakutrol in a gel solution.

In these implementations, Bakutrol can be solubilized to allow for a composition with enhanced acne treatment properties. As discussed above, when Bakutrol is solubilized, it can be effectively be absorbed into the skin to treat the skin. Research has shown that in a specific implementation of the composition, the product (a water-based acne gel), after applied to users' acne areas over several weeks, reduced inflammatory acne lesions by 50 percent in about 7 days with a 90 percent reduction achieved in 14 days. The product was also seen to work about three times faster than typical prescription and over-the-counter acne products. The results showed that the product does not cause collateral damage to the skin, including dry skin, skin irritation, redness, and peeling.

In these implementations, Bakutrol is stable in the product, while retaining its acne treatment properties. Some accelerated stability studies show that the product is stable for about one month to about 3 months at 25 degrees Celsius, 4 degrees Celsius, and 40 degrees Celsius, with no separation or precipitation. This correlates to about an 8 month to about 24 months shelf life.

The composition in these implementations is not limited to the specific ingredients presented. A composition of the invention may have additional compounds (not necessarily described in this application), different compounds which replace some of the compounds presented, fewer of the compounds presented, or any combination of these. For example, Bakutrol and bisabolol can be combined with other active ingredients (not presented above) such as benzoyl peroxide, retinoids (e.g., retinol and tretinoin), and antibiotics (e.g., erythromycin, clindamycin, and tetracycline), and the remainder is an emollient, water and other solvents. In these implementations, various ingredients other than those presented above can be used in combination with Bakutrol (e.g., other solvents such as caprylyl glycol, ethylhexylglycerin, PPG-2 isoceteth-20 acetate, and others).

Table A below provides the range of amount (percentage by weight) of each ingredient that can be used, while still maintaining its efficacy as an acne treatment agent. It should be understood that the invention is not limited to the specific percentages presented. A formulation of the invention may have additional compounds (not necessarily described in this application), different compounds which replace some of the compounds presented, fewer of the compounds presented, or any combination of these. Further, the compounds in other implementations of the invention may not be exactly the same as the compounds presented and may be modified or altered as appropriate for a particular application or based on the data or situation. For example, the percentages can also be specified by volume.

TABLE A

| Item Number | Ingredient | Range (Percentage by Weight (% WT/WT)) |
|---|---|---|
| 1 | Deionized Water | 40.00-80.00 |
| 2 | Hydroxyethylcellulose, Sodium Nitrate, Water (Natrosol 250 HHX Pharm) | 0.10-5.00 |
| 3 | Disodium EDTA (Dissolvine Na-2-P) | 0.01-1.00 |
| 4 | Sodium PCA, Water (Nalidone) | 0.10-5.00 |
| 5 | Butylene Glycol (1,3-Butylene Glycol) | 0.10-5.00 |
| 6 | Salicylic Acid (Curcylic SA 100) | 0.10-5.00 |
| 7 | Glycolic Acid, Water (Glypure 70) | 10.00-20.00 |
| 8 | Lactic Acid, Water (Purac HiPure 90) | 0.10-5.00 |
| 9 | Deionized Water | 5.00-15.00 |
| 10 | Sodium Hydroxide (Sodium Hydroxide, Pellets, NF) | 1.00-5.00 |
| 11 | Deionized Water | 0.10-5.00 |
| 12 | Dextrin, *Perilla Ocymoides* Leaf extract (Shiso Extract Powder) | 0.01-1.00 |
| 13 | Deionized Water | 0.10-5.00 |
| 14 | *Olea Europaea* Fruit Extract, Water (EurolBT) | 0.01-1.00 |
| 15 | Gluconolactone, Sodium Benzoate (Geogard Ultra) | 0.10-5.00 |
| 16 | Polysorbate 20 (Tween-20-LQ-(AP)) | 1.00-5.00 |
| 17 | Hydrolyzed *Psoralea Corylifolia* Extract (Bakutrol(TM)) | 0.01-1.00 |
| 18A | Bisabolol (Bisabolol RAC) | 0.01-1.00 |
| 18B | Caprylyl Glycol (Lexgard O) | 0.01-1.00 |
| 18C | Ethylhexylglycerin (Sensiva SC 50) | 0.01-1.00 |
| 18D | PPG-2 Isoceteth-20 Acetate (CUPL PIC) | 0.10-3.00 |

In specific implementations, a composition for an acne solution includes 0.01 percent to about 1 percent by weight of Bakutrol, and about 0.01 percent to about 1 percent by weight of bisabolol RAC. In a specific implementation, the ratio of Bakutrol to bisabolol RAC is about 12:1, 12.8:1 11:1, 11:5:1, 10:1, 10.1:1, 10.2:1 10.5:1, 10.8:1 9:1, 9.5:1, 9.7:1, 9.8:1, 9:9:1, 8:1, 8.25:1, or 8.5:1. In other implementations, this ratio can vary. The composition can include a greater amount of bisabolol than of Bakutrol. In these implementations, the ratio can be about 1:1, 1:2, 1:4, 1:6, 1:8, or 1:10.

In a specific implementation, the composition includes about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight of Bakutrol. Additionally, the composition can include about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent of bisabolol RAC. Bakutrol and bisabolol can be present in any combination of percentages, either individually or in combination.

Salicylic acid can be included in the composition in a range of about 0.10 percent to about 5.0 percent by weight. Salicylic acid is typically used to treat skin conditions including acne. The amount salicylic acid can vary in this range as appropriate for a particular application or based on the data or situation. In a specific implementation, the ratio of salicylic acid to Bakutrol is about 12:1, 12.8:1 11:1, 11:5:1, 10:1, 10.1:1, 10.2:1 10.5:1, 10.8:1 9:1, 9.5:1, 9.7:1, 9.8:1, 9:9:1, 8:1, 8.25:1, or 8.5:1. In other implementations, this ratio can vary. The composition can include a greater amount of Bakutrol than of salicylic acid. In these implementations, the ratio can be about 1:1, 1:2, 1:3, 1:4, 1:5, 1:6, 1:7, 1:8, 1:9 or 1:10. In a specific implementation, the composition includes about 0.5, 0.7, 0.75, 0.8, 0.85, 0.9, 0.95, 1.0, 1.05, 1.1, 1.15, 1.2, 1.25, 1.3, 1.35, 1.4, 1.5, 2.0, 2.5, 3.0, 4.0, or 5.0 percent by weight of salicylic acid.

In a specific implementation, the composition includes alpha hydroxy acid (AHA). In implementations, alpha hydroxy acid can include one or more of glycolic acid, lactic acid, malic acid, citric acid, tartaric acid, or suitable mixtures of two or more thereof. In a specific implementation, the composition includes about 10 percent to about 20 percent of glycolic acid, and 0.10 percent to about 5 percent of lactic acid. For example, glycolic acid is present in about 10.5, 11.5, 12.5, 13, 13.5, 13.8, 14.0, 14.1, 14.3, 14.5, 14.8, 15.0, 15.3, 15.8, 16.0, 16.5, or 17.0 percent, and lactic acid is present in about 0.15, 0.3, 0.5, 0.7, 0.75, 0.8, 0.9, 0.95, 1.0, 1.1, 1.3, 1.4, 1.6, 1.7, 2.0, 2.4, 2.9, 3.0, 3.5, or 4.0 percent. The amount of this combination of alpha hydroxy acids can be included individually or in combination.

The composition can include an extract derived from Perilla Ocymoides in an amount from about 0.01 to about 1.0 percent. For example, the amount of extract is about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight. In a specific implementation the extract is an extract power from shiso.

The composition can also include an extract derived from the Olea Europaea fruit, in an amount from about 0.01 to about 1.0 percent. For example, the amount of extract is about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight. The fruit is commonly called the olive.

The composition can include hydroxyethylcellulose in an amount from about 0.1 to about 5.0 percent. For example, the amount can be about 0.15, 0.3, 0.5, 0.7, 0.75, 0.8, 0.9, 0.95, 1.0, 1.1, 1.3, 1.4, 1.6, 1.7, 2.0, 2.4, 2.9, 3.0, 3.5, 4.0, 4.5, or 5.0 percent by weight.

Disodium EDTA can be included in an amount from about 0.01 to about 1 percent. For example, the amount of disodium EDTA is about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight.

Sodium PCA can be included in an amount from about 0.1 to about 5.0 percent. For example, the amount can be about 0.15, 0.3, 0.5, 0.7, 0.75, 0.8, 0.9, 0.95, 1.0, 1.1, 1.3, 1.4, 1.6, 1.7, 2.0, 2.4, 2.9, 3.0, 3.5, 4.0, 4.5, or 5.0 percent by weight.

The composition can include butylene glycol in an amount from about 0.1 to about 5.0 percent. For example, the amount can be about 0.15, 0.3, 0.5, 0.7, 0.75, 0.8, 0.9, 0.95, 1.0, 1.1, 1.3, 1.4, 1.6, 1.7, 1.9, 1.95, 2.0, 2.05, 2.1, 2.2, 2.3, 2.4, 2.9, 3.0, 3.5, 4.0, 4.5, or 5.0 percent by weight.

The composition can include sodium hydroxide in an amount from about 0.1 to about 5.0 percent. For example, the amount can be about 0.15, 0.3, 0.5, 0.7, 0.75, 0.8, 0.9, 0.95, 1.0, 1.1, 1.3, 1.4, 1.6, 1.7, 1.9, 1.95, 2.0, 2.05, 2.1, 2.2, 2.3, 2.4, 2.9, 3.0, 3.5, 4.0, 4.5, or 5.0 percent by weight.

The composition can include sodium benzoate in an amount from about 0.1 to about 5.0 percent. For example, the amount can be about 0.15, 0.3, 0.5, 0.7, 0.75, 0.8, 0.9, 0.95, 1.0, 1.1, 1.3, 1.4, 1.6, 1.7, 1.9, 1.95, 2.0, 2.05, 2.1, 2.2, 2.3, 2.4, 2.9, 3.0, 3.5, 4.0, 4.5, or 5.0 percent by weight. In a specific implementation, the composition includes sodium benzoate with gluconolactone.

The composition can include other ingredients including preservatives, thickeners, humectants, stabilizers, buffers, emollients, emulsifying agents, and water. In a specific implementation, the composition includes about 1 percent to about 5 percent by weight of polysorbate 20. For example, an amount of about 1.0, 1.1, 1.3, 1.4, 1.6, 1.7, 1.9, 1.95, 2.0, 2.05, 2.1, 2.2, 2.3, 2.4, 2.9, 3.0, 3.5, 4.0, 4.5, or 5.0 percent by weight is included.

In other implementations, polysorbate 20 can be substituted with 0.01 percent to about 1 percent of caprylyl glycol. For example, an amount of about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight is included. In another specific implementation, caprylyl glycol can be substituted with 0.01 percent to about 1 percent of ethylhexylglycerin. For example, an amount of about 0.01, 0.015, 0.02, 0.025, 0.03, 0.035, 0.05, 0.06, 0.07, 0.075, 0.09, 0.1, 0.2, 0.25, 0.3, 0.4, 0.5, 0.6, 0.7, 0.8, 0.9, or 1.0 percent by weight is included. And in yet another specific implementation, ethylhexylglycerin can be substituted with 0.1 percent to about 3 percent of PPG-2 isoceteth-20 acetate. For example, an amount of about 0.15, 0.3, 0.5, 0.7, 0.75, 0.8, 0.9, 0.95, 1.0, 1.1, 1.3, 1.4, 1.6, 1.7, 1.9, 1.95, 2.0, 2.05, 2.1, 2.2, 2.3, 2.4, 2.9, or 3.0 percent by weight is included. In these other implementations, other ingredients' weight by percentage can be adjusted accordingly. For example, in a composition using 1.00 percent PPG-2 isoceteth-20 acetate, an amount of deionized water can be increased or decreased accordingly.

The amount of water in the final composition can be from about 45 to about 99 percent. For example, in a specific implementation, deionized water is included in an amount of about 70, 70.5, 70.3, 70.9, 72.5, 72.9, 73.0, 73.1, 73.3, 73.4, 73.5, 73.6, 73.7, 73.9, 80.1, 80.15, 80.2, or 81.0 percent by weight.

The composition can be formulated as a water-based, topical gel. In a specific implementation, the gel is a semiviscous gel solution. The solution can have a specific gravity from about 1.06 to 1.10, about 17.5 percent to about 21.5 percent of solids, a viscosity of about 4000 to about 8000 centipoise (cps), and a pH of about 3.5 to about 4.5.

The composition can be included in a cleanser, cream, lotion, serum, essence, balm, or an emulsion (e.g., an oil-in-water emulsion or a water-in-oil emulsion). For example, the composition can be included in a group of products (e.g., day cream, night cream, cleanser, toner, and acne gel), prescribed for use together, in order to maximize the acne treatment properties of the composition. The composition can be alcohol-free or substantially alcohol-free. Formulations can include more or less humectants, oils, botanicals, or other ingredients where the composition is adjusted for different skin types (e.g., dry, oily, acne prone, combination, dull, sensitive, or aging skin).

The present invention includes a method of preparation of a water-based acne gel composition. The preparation solubilizes Bakutrol and allows it to be stable in the gel.

The procedure listed below in Table B provides a specific example of a preparation of a water-based acne gel including solubilized Bakutrol. The item numbers presented in Table B are the item numbers as presented in Table A above. The amount of each item is according to the ranges presented in Table A, and in the specific implementations provided above. It should be understood that the invention is not limited to the specific percentages presented. A formulation of the invention may have additional compounds (not necessarily described in this application), different compounds which replace some of the compounds presented, fewer of the compounds presented, or any combination of these. Further, the compounds in other implementations of the invention may not be exactly the same as the compounds presented and may be modified or altered as appropriate for a particular application or based on the data or situation. For example, the percentages can also be specified by volume.

It should further be understood that the invention is not limited to the specific steps presented below. A preparation of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or based on the data or situation.

TABLE B

| Step Number | |
|---|---|
| 1 | Into a first processing tank, equipped with a propeller mixer and side sweep, add item #1 (deionized water). Begin high speed mixing. |
| 2 | Sprinkle in item #2. Mix until completely uniform and free of lumps. |
| 3 | Heat to 70-75 degrees Celsius. Add item #3 and item #4. Mix until uniform. Cool to 60-65 degrees Celsius. |
| 4 | In a separate vessel, add item #5 and item #6. Heat to 60-65 degrees Celsius until uniform. Add to the first processing tank. Mix until completely uniform. Cool to 55-60 degrees Celsius. |
| 5 | Add item #7 and item #8. Mix until uniform. Cool to 50-55 degrees Celsius. |
| 6 | Premix item #9 and item #10. Slowly add to the first processing tank. Mix until uniform. Cool to 45-50 degrees Celsius. |
| 7 | Premix item #11 and item #12. Add to the first processing tank. Mix until uniform. |
| 8 | Premix item #13 and item #14. Add to the first processing tank. Mix until uniform. Cool to 40-45 degrees Celsius. |
| 9 | Add item #15. Mix until uniform. |
| 10 | Premix item #16, item #17, and item #18A. Add to the first processing tank. Mix until completely uniform. |
| 11 | QS batch with deionized water if necessary. Continue mixing and cooling to 35 degrees Celsius. |

In another specific implementation, in step 10, item #18A (polysorbate 20) can be substituted with an amount of caprylyl glycol (item #18B), while the other steps and ingredients are the same as presented in Table B. In another specific implementation, in step 10, caprylyl glycol can be substituted with an amount of ethylhexylglycerin (item #18C). And in yet another specific implementation, in step 10, ethylhexylglycerin can be substituted with an amount of PPG-2 isoceteth-20 acetate (item #18D). In these other implementations, other ingredients' weight by percentage can be adjusted accordingly. For example, in a composition using 1.0 percent PPG-2 isoceteth-20 acetate, an amount of deionized water can be decreased or increased accordingly.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method of preparing an aqueous mixture comprising:
    mixing deionized water and hydroxyethylcellulose to obtain a first mixture;
    applying heat to the first mixture until the first mixture reaches about 75 degrees Celsius;
    adding disodium ethylenediaminetetraacetic acid (EDTA) and sodium pyrrolidone carboxylic acid (PCA) to the first mixture and mixing to obtain a second mixture;
    allowing the second mixture to cool to from about 60 to 65 degrees Celsius;
    mixing butylene glycol and salicylic acid to obtain a third mixture;
    applying heat to the third mixture until the third mixture reaches about 65 degrees Celsius;
    mixing the third mixture and second mixture together to obtain a fourth mixture;
    allowing the fourth mixture to cool to from about 55 to 60 degrees Celsius;
    adding glycolic acid and lactic acid to the fourth mixture and mixing to obtain a fifth mixture;
    allowing the fifth mixture to cool to from about 50 to 55 degrees Celsius;
    mixing deionized water and sodium hydroxide to obtain a sixth mixture;
    mixing the sixth mixture and the fifth mixture together to obtain a seventh mixture;
    allowing the seventh mixture to cool to from about 45 to 50 degrees Celsius;
    mixing deionized water and perilla ocymoides leaf extract to obtain an eighth mixture;
    mixing the eighth mixture and the seventh mixture to obtain a ninth mixture;
    mixing deionized water and olea europaea fruit extract to obtain a tenth mixture;
    mixing the tenth mixture and ninth mixture to obtain an eleventh mixture;
    allowing the eleventh mixture to cool to from about 40 to 45 degrees Celsius;
    adding sodium benzoate to the eleventh mixture and mixing to obtain a twelfth mixture;
    solubilizing an unsolubilized hydrolyzed *Psoralea Corylifolia* extract to obtain a solubilized hydrolyzed *Psoralea Corylifolia* extract comprising mixing the unsolubilized hydrolyzed *Psoralea Corylifolia* extract, bisabolol, and polysorbate 20 to obtain a thirteenth mixture, and adding the thirteenth mixture to the twelfth mixture at a temperature from 40 to 45 degrees Celsius to obtain a fourteenth mixture, wherein the fourteenth mixture comprises the solubilized hydrolyzed *Psoralea Corylifolia* extract;
    allowing the fourteenth mixture to cool to about 35 degrees Celsius; and
    obtaining an aqueous mixture that is a combination of the twelfth and thirteenth mixtures, wherein the aqueous mixture comprises an oil-free, water-based, anti-acne gel.

2. The method of claim 1 comprising:
    adding benzoyl peroxide to the polysorbate 20, bisabolol, and hydrolyzed *Psoralea Corylifolia* extract of the thirteenth mixture.

3. The method of claim 1 wherein the aqueous mixture comprises at least one of a retinoid or an antibiotic.

4. The method of claim 1 wherein the hydrolyzed *Psoralea Coryliolia* extract comprises bakuchiol.

5. The method of claim 1 wherein the thirteenth mixture does not comprise an alcohol constituent.

6. A method of preparing a water-based mixture comprising:
    mixing deionized water and hydroxyethylcellulose to obtain a first mixture;
    applying heat to the first mixture until the first mixture reaches about 75 degrees Celsius;
    adding disodium ethylenediaminetetraacetic acid (EDTA) and sodium pyrrolidone carboxylic acid (PCA) to the first mixture and mixing to obtain a second mixture;
    allowing the second mixture to cool to from about 60 to 65 degrees Celsius;
    mixing butylene glycol and salicylic acid to obtain a third mixture;
    applying heat to the third mixture until the third mixture reaches about 65 degrees Celsius;
    mixing the third mixture and second mixture together to obtain a fourth mixture;
    allowing the fourth mixture to cool to from about 55 to 60 degrees Celsius;
    adding glycolic acid and lactic acid to the fourth mixture and mixing to obtain a fifth mixture;
    allowing the fifth mixture to cool to from about 50 to 55 degrees Celsius;
    mixing deionized water and sodium hydroxide to obtain a sixth mixture;
    mixing the sixth mixture and the fifth mixture together to obtain a seventh mixture;
    allowing the seventh mixture to cool to from about 45 to 50 degrees Celsius;
    mixing deionized water and perilla ocymoides leaf extract to obtain an eighth mixture;
    mixing the eighth mixture and the seventh mixture to obtain a ninth mixture;
    mixing deionized water and olea europaea fruit extract to obtain a tenth mixture;
    mixing the tenth mixture and ninth mixture to obtain an eleventh mixture;
    allowing the eleventh mixture to cool to from about 40 to 45 degrees Celsius;
    adding sodium benzoate to the eleventh mixture and mixing to obtain a twelfth mixture;
    solubilizing an unsolubilized bakuchiol to obtain a solubilized bakuchiol comprising mixing the unsolubilized bakuchiol, bisabolol, and polysorbate 20 to obtain a thirteenth mixture, and adding the thirteenth mixture to the twelfth mixture at a temperature from 40 to 45 degrees Celsius to obtain a fourteenth mixture, wherein the fourteenth mixture comprises the solubilized bakuchiol;

allowing the fourteenth mixture to cool to about 35 degrees Celsius, and obtaining a water-based mixture that is a combination of the twelfth and thirteenth mixtures, wherein the water-based mixture does not comprise an oil constituent.

7. The method of claim 6 wherein the thirteenth mixture does not comprise an alcohol constituent.

8. The method of claim 6 wherein a ratio of an amount of bakuchiol to an amount of bisabolol is about 10:1.

9. The method of claim 6 wherein a ratio of an amount of salicylic acid to an amount of bakuchiol is about 10:1.

10. A method of preparing a water-based mixture comprising:

mixing deionized water and hydroxyethylcellulose to obtain a first mixture;

applying heat to the first mixture until the first mixture reaches about 75 degrees Celsius;

adding disodium ethylenediaminetetraacetic acid (EDTA) and sodium pyrrolidone carboxylic acid (PCA) to the first mixture and mixing to obtain a second mixture;

allowing the second mixture to cool to from about 60 to 65 degrees Celsius;

mixing butylene glycol and salicylic acid to obtain a third mixture;

applying heat to the third mixture until the third mixture reaches about 65 degrees Celsius;

mixing the third mixture and second mixture together to obtain a fourth mixture;

allowing the fourth mixture to cool to from about 55 to 60 degrees Celsius;

adding glycolic acid and lactic acid to the fourth mixture and mixing to obtain a fifth mixture;

allowing the fifth mixture to cool to from about 50 to 55 degrees Celsius;

mixing deionized water and sodium hydroxide to obtain a sixth mixture;

mixing the sixth mixture and the fifth mixture together to obtain a seventh mixture;

allowing the seventh mixture to cool to from about 45 to 50 degrees Celsius;

mixing deionized water and perilla ocymoides leaf extract to obtain an eighth mixture;

mixing the eighth mixture and the seventh mixture to obtain a ninth mixture;

mixing deionized water and olea europaea fruit extract to obtain a tenth mixture;

mixing the tenth mixture and ninth mixture to obtain an eleventh mixture;

allowing the eleventh mixture to cool to from about 40 to 45 degrees Celsius;

adding sodium benzoate to the eleventh mixture and mixing to obtain a twelfth mixture;

solubilizing an unsolubilized hydrolyzed *Psoralea Corylifolia* extract to obtain a solubilized hydrolyzed *Psoralea Corylifolia* extract comprising mixing the unsolubilized hydrolyzed *Psoralea Corylifolia* extract, bisabolol, and polysorbate 20 to obtain a thirteenth mixture, and adding the thirteenth mixture to the twelfth mixture at a temperature from 40 to 45 degrees Celsius to obtain a fourteenth mixture, wherein the fourteenth mixture comprises the solubilized hydrolyzed *Psoralea Corylifolia* extract;

allowing the fourteenth mixture to cool to about 35 degrees Celsius, and obtaining a water-based mixture that is a combination of the twelfth and thirteenth mixtures, wherein the thirteenth mixture does not comprise an alcohol constituent.

11. The method of claim 10 wherein the first compound comprises polysorbate 20.

12. The method of claim 10 wherein the first compound comprises caprylyl glycol.

13. The method of claim 10 wherein the first compound comprises ethylhexylglycerin.

14. The method of claim 10 wherein the first compound comprises PPG-2 isoceteth-20 acetate.

15. The method of claim 10 wherein the water-based mixture does not include an oil constituent.

* * * * *